United States Patent [19]

Wang

[11] 4,265,912

[45] May 5, 1981

[54] GLAUCINE LACTATE SALTS

[75] Inventor: Samuel S. M. Wang, Indianapolis, Ind.

[73] Assignee: The Dow Chemical Company, Midland, Mich.

[21] Appl. No.: 93,648

[22] Filed: Nov. 13, 1979

Related U.S. Application Data

[63] Continuation of Ser. No. 935,220, Aug. 21, 1978, abandoned.

[51] Int. Cl.$^3$ .................. A61K 31/485; C07D 221/18; C07D 221/22
[52] U.S. Cl. ........................................ 424/260; 546/71
[58] Field of Search ....................... 260/286 R; 546/71

[56] References Cited

FOREIGN PATENT DOCUMENTS 866079 4/1978 Belgium .

OTHER PUBLICATIONS

Chem. Pharm. Bull., vol. 18, pp. 1219–1223, 1224–1227 (1970).
Donev, Farmatsiya (Sofia) 12(4), 17–21 (1962) + 14(2), 49–54 (1964).

*Primary Examiner*—Stanley J. Friedman

[57] ABSTRACT

Novel lactate salts of 1 and d,l-glaucine are prepared by reacting 1 or d,l-glaucine base with lactic acid. The glaucine salts have potent analgesic and antitussive properties, excellent flavor characteristics and stability properties. Pharmaceutical compositions, and methods of using the same are also described.

8 Claims, No Drawings

GLAUCINE LACTATE SALTS

CROSS REFERENCE TO RELATED APPLICATION

This is a continuation of application Ser. No. 935,220, filed Aug. 21, 1978, now abandoned.

BACKGROUND OF THE INVENTION

Dextro-rotary glaucine or d-glaucine hydrobromide has been used as an antitussive agent. D-glaucine can be isolated from the yellow poppy. The racemate, d,l-glaucine can be synthesized from papaverine, following the procedure of Frank and Tietze, Angewandte Chemie (1967) pp 815–6. A variety of other preparative procedures are also known. Cham and Maitland, J. Org. Chem. J. Chem. Soc. (C) 1966, 753; and Cava, et al. J. Org. Chem. 35, 175 (1970). Separation of the isomers has been carried out by conventional procedures, such as using d or l-tartaric acid to form the d- or l-tartrate salts and separating the salts by fractional crystallization.

Glaucine has the structure

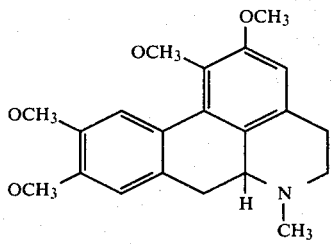

and is thus structurally related to other plant alkaloids such as codeine and aporphine.

Codeine, and related compounds such as hydrocodone, dihydrocodeine and dextromethorphan are well known as antitussive agents. Merck Index, Ninth Ed., Merck & Co., Rahway, N.J. (1976) monographs Nos. 2420-24, 3148 4672, and 7908. Although these compounds are also well known to have a high potential for habituation or addiction, they remain the most potent and widely used antitussive agents. Codeine, hydrocodone, and dihydrocodeine have also been used as narcotic analgesics.

Antitussive agents are usually administered orally, most typically in the form of a liquid formulation such as an elixir, suspension or syrup, or in a solid lozenge or cough drop which is held in the mouth until it dissolves. In both cases the unpleasant bitter flavor of the alkaloid is known disadvantage of such agents. Various formulations have been developed to mask the unpleasant taste and after taste of codeine, dihydrocodeine and dextromethorphan, with varying degrees of success. None of these techniques have been completely successful. Glaucine, like codeine, has an unpleasant bitter taste.

SUMMARY OF THE INVENTION

This invention is directed to the lactate salts of l-glaucine and d,l-glaucine, to pharmaceutical compositions containing said salts and to methods for using them as antitussive agents.

It has now been found that l- and d,l-glaucine lactate have antitussive properties that are unexpectedly superior to the d-glaucine, and that d,l and l-glaucine lactate salts have desirable solubility and stability properties, unexpected flavor and palatability properties, analgesic activity, and low addictive potential.

The novel lactate salts of the invention are crystalline solids which are prepared by reacting l-glaucine or d,l-glaucine (or mixtures thereof) in the form of the base, with lactate ion under conditions adapted to the formation of lactate salts of organic bases. The salts can be obtained in crystalline solid form.

The compounds can be readily prepared by reacting the free glaucine base with lactic acid. The reaction proceeds readily in the presence of an inert organic solvent, such as acetone, ethanol, chloroform methanol, or diethyl ether, or ethyl acetate. The lactate salt typically forms as a precipitate, which can be recovered by conventional techniques such as filtration or decantation and purified by conventional steps such as recrystallization and washing.

The reaction is typically carried out by dissolving the free base glaucine in the inert organic solvent at a temperature from ambient temperature to the boiling point of the mixture, and adding an equimolar amount or an excess of lactic acid. Lactic acid can be employed in from about 0.5 to about 1 to 2 to 3 fold molar excess or more. Use of equimolar amounts is preferred.

When using excess lactic acid the excess latic acid precipitating with the product can be removed by re-crystallization.

Mixtures of the l- and d,l-glaucine lactate, l-glaucine lactate salts, and the racemic salt are all useful as antitussive agents and analgesic agents, with similar desirable properties. For convenience it is generally preferred to use a single lactate salt, such as the d,l-glaucine lactate or l-glaucine lactate, the preferred salt being d,l-glaucine lactate.

The glaucine lactate salts are highly effective, orally active antitussive agents and also have analgesic activity when administered orally, combined with surprising palatability and desirable stability and solubility, and a useful freedom from undesired side effects, such as addictive properties. They can be administered at dosages of from about 0.1 to about 40 milligrams or more per kilograms (mg/kg) for antitussive effect, and from about 0.1 to about 60 mg/kg for analgesic use, preferably by oral administration. They are also active parenterally as antitussives and analgesics, by intraperitoneal injection, for example.

In practicing the method of the invention, an antitussive amount of one or more of the glaucine lactates is administered internally to an animal, typically a mammal in need thereof. Administration can be carried out either by a parenteral route, such as by intravenous, intraperitoneal, or intramuscular injection, or by introduction into the gastrointestinal tract via oral or rectal administration, for example, or by oral administration of a glaucine lactate solution in the form of a throat spray, for example.

The antitussive amount of the compound, that is, the amount of the glaucine lactate sufficient to inhibit or alleviate coughing depends on various factors such as the size, type and age of the animal to be treated, the particular salt or mixture of salts employed, the route and frequency of administration, the severity of cough (if any) and the causative agent involved and the time of administration. Similar considerations apply to selection of an analgesic dose for administration to animals. The glaucine lactate salts are generally effective when administered orally as well as in parenteral dosages. For example, in antitussive evaluations in which codeine phosphate has an $ED_{50}$ of 10.9 mg/kg by intraperitoneal injection and an oral $ED_{50}$ of 86.6 mg/kg, the oral and intraperitoneal $ED_{50}$'s obtained with d,l-glaucine lactate are 63.4 and 7.9 mg/kg. In particular case, the dosage to be administered can be ascertained by conventional range finding techniques, for example, by observing the antitussive activity produced at different dosage rates.

Good antitussive results can be obtained when the salts are administered orally at dosage rates from about 0.1 to about 0.2, to about 0.5 to about 1 to about 10 to about 20 to 25 to 30 to 40 to about 80 milligrams of glaucine salt compound per kilogram of animal body weight and at rates of 0.1 to 40 mg/kg by intraperitoneal injection. It is generally desirable to administer individual dosages at the lowest amount which provides the desired cough suppression consonant with a convenient dosing schedule. Oral administration is the route generally preferred for administration of antitussive agents. The glaucine lactates of the invention thus combine high oral antitussive potency with palatability, making them particularly useful orally.

Dosage units adaptable to oral administration such as tablets, capsules, lozenges, elixirs, syrups and the like are preferred and the active glaucine lactate compound can be formulated in conventional timed release capsule or tablet formulations.

In using the compounds of the invention, the active glaucine lactate ingredient is preferably incorporated in a composition comprising a pharmaceutical carrier and from about 0.001 to about 95 percent by weight of the glaucine lactate salt compound. The term "pharmaceutical carrier" refers to known pharmaceutical excipients useful in formulating pharmacologically-active compounds for internal administration to animals, and which are substantially non-toxic and non-sensitizing under conditions of use. The compositions can be prepared by known techniques for the preparation of tablets, capsules, cough drops, lozenges, troches, suppositories, solutions, elixirs, syrups, emulsions, dispersions, wettable and effervescent powders, sterile injectable compositions, and can contain suitable excipients known to be useful in the preparation of the particular type of composition desired.

The compounds may be administered in conjunction with other active ingredients or other antitussive or analgesic agents. Other active ingredients can include, for example, antihistamines, decongestants, expectorants, mucolytic agents, bronochodilators and antibacterial agents or local anesthetics. Combinations of this type are generally useful for treating coughing or pain in combination with other symptoms.

Particularly desirable compositions are those prepared in the form of dosage units, such as solid forms, including troches, lozenges, tablets, capsules, or measured volumes of liquid compositions, containing from about 0.1 milligram to about 20 to 30 milligrams of the glaucine salt per unit, for antitussive use and from about 0.1 milligram to about 30 to about 60 milligrams for analgesic use.

EXAMPLE 1

Preparation of d,l-Glaucine Lactate

A. Two grams of d,l-glaucine was dissolved in 40 milliliters absolute alcohol (ethanol) at a temperature of 50° C., and the solution was added, with stirring, to a solution of 0.57 grams of 85 percent lactic acid diluted with 5 milliliters of ethanol. The resulting mixture was concentrated under vacuum, cooled; and diethyl ether was added to the concentrated solution until a precipitate formed. The white crystalline solid precipitate was collected by filtration and washed with diethyl ether. The d,l-glaucine lactate product (1.5 gram yield) was found to melt at 148.6°–151° C. After recrystallization from ethanol-diethyl ether, the purified salt was found to melt at 153.3° C. The product evidenced no optical rotation. ($[\alpha]_D^{25} = 0.0°$ in water—100 mg/20 ml.

B. 5.6 Grams (0.02 mole) of d,l-glaucine was dissolved in 30 ml of alcohol USP (95 percent ethanol, 5 percent water). A solution of 2.5 grams (0.02 mole) of 85 percent d,l-lactate acid ($[\alpha]_D = 0$) in 50 ml of alcohol USP was added to the glaucine solution with stirring. The solution was concentrated under reduced pressure, cooled in a refrigerator, and dry diethyl ether was added until crystal formation was complete. The crystalline product was separated by filtration, washed with diethyl ether, and found to melt at 147°–151° C. (Yield 7.3 grams, 100 percent) The d,l-glaucine-d,l-lactate product was dissolved in 130 ml alcohol USP at about 60° C., filtered, and cooled. Diethyl ether was added to precipitate the product, and the purified d,l-glaucine-d,l-lactate was found to melt at 153° C. (Yield 96 percent; assay 99.8 percent pure.)

C. Elemental analysis of d,l-glaucine lactate: C,H,N-calculated 64.70, 7.01, 3.14; C,H,N-found 62.19, 7.17, 3.02.

EXAMPLE 2

Separate groups of guinea pigs were orally administered various doses of a test compound, or distilled water for a control group. One hour after oral dosing, the guinea pigs were exposed to a 5 percent aerosol of citric acid for a 10 minute test period. The number of cough responses produced during the last five minutes of exposure to the citric acid aerosol was recorded and the dosage effect to suppress coughing in 50 percent of the guinea pigs ($ED_{50}$) was calculated. An antitussive effect was recorded for a guinea pig when its total number of coughs during the 5 minute test period were at least two standard deviation units below the mean number of coughs per guinea pig in the control group. In these operations, codeine phosphate was found to have an oral $ED_{50}$ of 86.6; d-glaucine hydrobromide an $ED_{50}$ of 89.0; and d,l-glaucine lactate an $ED_{50}$ of 63.4 milligrams per kilogram.

EXAMPLE 3

In an operation similar to that of Example 2, test compounds were administered to guinea pigs by intraperitoneal injection, with one group of guinea pigs receiving distilled water as a control. $ED_{50}$'s were calculated for antitussive activity in the citric acid aerosol test as described in Example 2. Codeine phosphate was found to have an $ED_{50}$ of 10.9 mg/kg; d-glaucine hydrobromide an $ED_{50}$ of 10.0 mg/kg; and d,l-glaucine lactate an $ED_{50}$ of 7.9 mg/kg.

EXAMPLE 4

A cough syrup vehicle formulation was prepared containing the following pharmaceutically-acceptable excipients:

| Excipient | Amount |
| --- | --- |
| Sugar (cane) | 1600 grams |

| Excipient | Amount |
| --- | --- |
| Sorbitol solution USP | 600 grams |
| Ethanol (Alcohol USP) | 21 grams |
| Water | q.s. to 4 liters total |

The solubility of d,l-glaucine hydrobromide in this cough syrup vehicle was found to be 0.3 percent, or about 15 milligrams in a 5 milliliter dosage unit. The solubility of d,l-glaucine lactate was found to be 2 percent, or about 100 milligrams per 5 milliliter dosage unit.

EXAMPLE 5

Stability of d,l-glaucine lactate was examined in the syrup vehicle of Example 4. After one month at ambient temperature, 40° C. and 55° C., respectively, syrup formulated to contain 0.6 percent d,l-glaucine lactate was found to retain 98.8, 100.6 and 96.7 percent, respectively, of the original glaucine concentration.

Syrups containing codeine phosphate, 0.2 percent, contained 97.5, 104.5 or 100 percent, respectively, after one month at ambient temperature, 40° C. or 55° C. Syrups containing d,l-glaucine hydrobromide, 0.2 percent, resulted in assays of 99, 96 and 89.5 percent, respectively, after one month at ambient temperature, 40° C. and 55° C. After three months, the percentage amount of antitussive agent remaining was as shown below

| Compound | Percentage Remaining after 3 months at | | |
| --- | --- | --- | --- |
|  | Ambient | 40° C. | 55° C. |
| d,l-Glaucine Lactate | 104.1 | 97.0 | 97.4 |
| Codeine Phosphate | 101.3 | 101.1 | 88.4 |
| d,l-Glaucine . HBr | 100.8 | 93.3 | 91.4 |

EXAMPLE 6

In a procedure similar to that of Example 5, syrup formulations were prepared, placed in amber glass bottles and transparent (flint) glass bottles, and held under conditions of ambient temperature with continuous exposure to light. (About 2000 Foot-candles of combined fluorescent and incandescent light, for 24 hours/day.)

After one month, the d,l-glaucine hydrobromide assay of amber bottles was 84 percent, that of flint glass bottles was 74.5 percent. D,l-glaucine lactate in amber glass had an assay of 94 percent, in flint glass 80.6 percent. Codeine phosphate appeared stable in both types of container, with assays of 100 percent.

In other operations, crystalline d,l-glaucine lactate was found to retain over 99 percent of its original assay after 2 months storage at 40° C.

EXAMPLE 7

Physical dependency liability was evaluated in mice by the procedure of Saelens, et al., Arch. Int. Pharmacodynam, 190:213-218, 1971. In this procedure, mice are administered increasing doses of a test compound at intervals on two consecutive days. The last dosage on the second day is followed by intraperitoneal injection of the morphine antagonist, naloxone, at a dosage of 100 mg/kg, and the mice are observed for characteristic jumping behaviour indicative of opiate withdrawals or morphine antagonism. In these operations, morphine sulfate produced stimulation and Straub tail in mice, followed by jumping in 5 of 9 mice (96 jumps total) after naloxone treatment. Codeine phosphate produced Straub tail and stimulation, and naloxone-induced jumping in 2 of 6 mice (23 jumps total). d,l-Glaucine lactate (2:3) produced no Straub tail at the highest dose (100 mg/kg) and no jumping behaviour in any of the ten mice tested.

EXAMPLE 8

Several d,l-glaucine salts were prepared as 0.2 percent (weight by volume) solutions in distilled water. The various salt solutions were evaluated for palatability by touching a few drops to the tongue. In these operations, which included blind sampling by a trained flavor formulator experienced in flavoring of formulations containing agents such as codeine and dextromethorphan, the hydrobromide was characterized as objectionable with a bitter, sharp and metallic initial taste which increased with time. The sulfate, maleate, citrate, acetate, and p-toluenesulfonate salts were similar to the hydrobromide and similarly objectionable. The salicylate and succinate salts were ranked as more objectionable than the hydrobromide. d,l-Glaucine lactate was found to lack the sharp, metallic flavor and to be unobjectionable.

EXAMPLE 9

A. A flavored cough syrup formulation is prepared to contain the following:

| Ingredient | Amount |
| --- | --- |
| Sucrose (100% Invert Sugar-Dry Basis) | 26.4 Grams |
| Sorbitol Syrup USP | 10 Milliliters (Ml) |
| Glycerine | 5 Ml |
| Alcohol USP | 5.4 Ml |
| Piperonal | 10.0 Milligrams (Mg) |
| Vanillin | 7.5 Mg |
| Ethyl Vanillin | 10.0 Mg |
| Ethyl Maltol | 7.5 Mg |
| l-Menthol | 7.5 Mg |
| d,l-Glaucine Lactate | 600 Mg |
| Purified Water USP | Q.s. to 100 Ml Total |

The syrup contains 0.6 percent (weight by volume), d,l-glaucine lactate and a 5 ml. dosage unit (1 teaspoon) contains 30 mg of active lactate salt. The syrup can be sealed into 5 ml plastic lined foil pouches, or filled into conventional glass bottles. Dosage units of 15 mg and 20 mg per 5 ml dose can be made by using 300 or 400 mg of d,l-glaucine lactate or l-glaucine lactate or mixtures thereof in the above formula.

B. Tablets are prepared as follows: 40 grams l-glaucine lactate; 150 grams of modified starch (Sta-Rex 1500) are mixed and granulated with sufficient aqueous alcohol (75 percent water, 25 percent ethanol) to prepare a granulation. The granulation is dried and mixed with 15 gram starch USP; 1.5 grams stearic acid (40 mesh); 0.5 grams hydrogenated vegetable oil (40 mesh) 3 grams colloidal silicon dioxide and microcrystalline cellulose q.s. to 300 grams. The ingredients are mixed and compressed into 300 milligram tablets using 11/32 inch tablet dies. The tablets contain 40 milligrams of l-glaucine lactate each.

C. Capsules are prepared by blending 10 grams d,l-glaucine lactate, 3 grams colloidal silica; 2 grams stearic acid and 285 grams lactose; and filling the blend into No. 2 gelatin capsules, 300 milligrams per capsule. This provides 10 milligrams of glaucine lactate per capsule. Larger unit dosages, such as 15, 20 or 25 mg, can be prepared by using 15, 20 or 25 grams glaucine lactate and lactose q.s to 300 grams. Smaller dosages are similarly prepared.

D. Troches are prepared by mixing 30 grams d,l-glaucine lactate 435 grams powdered sugar and 35 grams powdered acacia; adding sufficient water to form a pliable mass; rolling the mass into a cylindrical shape and dividing the mass into 0.5 gram segments.

EXAMPLE 10

In other operations, various dosages of d,l-glaucine lactate were administered to groups of mice by the oral route or by intraperitoneal injection, and the dosage which is lethal to 50 percent of the mice ($LD_{50}$) was calculated from the mortality observations within 72 hours after administration. The $LD_{50}$ for intraperitoneal injection was found to be 178 mg/kg. The oral $LD_{50}$ in these operations was found to be 383 mg/kg.

EXAMPLE 11

Test compounds were evaluated for analgesic activity in the phenyl-p-quinone mouse writhing test of Hendershot & Forsaith, J. Pharmacol. Exptl. Therap. 125(3) 237 (1959). The test compounds were administered orally 30 minutes prior to the phenyl-p-quinone challenge. In these operations, the oral $ED_{50}$+s for d-glaucine hydrobromide, codeine phosphate, and d,l-glaucine lactate were found to be 34.0, 21.2 and 25.5 mg/kg respectively.

What is claimed is:

1. A glaucine salt selected from the group consisting of l-glaucine lactate, d,l-glaucine lactate and mixtures thereof.

2. Compound of claim 1 wherein the compound is d,l-glaucine lactate.

3. A composition comprising from about 0.01 percent by weight to about 95 percent by weight of a glaucine lactate compound selected from the group consisting of l-glaucine lactate, d,l-glaucine lactate and mixtures thereof, in admixture with a pharmaceutical carrier.

4. Composition of claim 3 wherein the composition is in dosage unit form adapted for oral administration as an antitussive agent, and wherein the compound contains from about 0.1 to about 90 milligrams of the glaucine lactate per unit.

5. Composition of claim 3 or 4 wherein the compound is d,l-glaucine lactate.

6. A method of alleviating coughing in animals, comprising administering to an animal an antitussive amount of a glaucine salt selected from the group consisting of l-glaucine lactate, d,l-glaucine lactate and mixtures thereof.

7. Method of claim 6 wherein the compound is d,l-glaucine lactate.

8. Method of claim 6 wherein the compound is administered orally.

* * * * *

UNITED STATES PATENT AND TRADEMARK OFFICE
CERTIFICATE OF CORRECTION

PATENT NO. : 4,265,912
DATED : May 5, 1981
INVENTOR(S) : Samuel S. M. Wang

It is certified that error appears in the above-identified patent and that said Letters Patent are hereby corrected as shown below:

Column 7, line 29, "$ED_{50}+s$" should read --$ED_{50}$'s--.

Column 8, line 1, "21.2" should read --21.1--.

Signed and Sealed this

Thirtieth Day of March 1982

[SEAL]

Attest:

GERALD J. MOSSINGHOFF

Attesting Officer    Commissioner of Patents and Trademarks